United States Patent
Nagano et al.

(10) Patent No.: US 7,102,027 B2
(45) Date of Patent: Sep. 5, 2006

(54) ADAMANTANETRICARBOXYLIC ACID DERIVATIVES

(75) Inventors: Shinya Nagano, Himeji (JP); Jiichiro Hashimoto, Himeji (JP)

(73) Assignee: Daicel Chemical Industries, Ltd., Osaka (JP)

( * ) Notice: Subject to any disclaimer, the term of this patent is extended or adjusted under 35 U.S.C. 154(b) by 234 days.

(21) Appl. No.: 10/807,284

(22) Filed: Mar. 24, 2004

(65) Prior Publication Data

US 2004/0242923 A1 Dec. 2, 2004

(30) Foreign Application Priority Data

Mar. 26, 2003 (JP) ............................. 2003-086166

(51) Int. Cl.
C07C 69/753 (2006.01)
C07C 61/15 (2006.01)
C07C 233/58 (2006.01)
C07D 307/20 (2006.01)
C07F 7/18 (2006.01)
C07D 403/14 (2006.01)

(52) U.S. Cl. .................. 560/117; 548/517; 548/525; 548/528; 549/420; 549/475; 558/442; 562/499; 562/853; 564/152; 564/153; 564/180

(58) Field of Classification Search ........... 560/127, 560/117; 548/517, 525, 528; 549/420, 475; 558/442; 562/499, 853; 564/152, 153, 180
See application file for complete search history.

(56) References Cited

U.S. PATENT DOCUMENTS 6,392,104 B1 * 5/2002 Ishii et al. .................. 568/818

FOREIGN PATENT DOCUMENTS

| EP | 0 915 077 A1 | 5/1999 |
|---|---|---|
| JP | 62-183881 A | 8/1987 |
| JP | 2001-332543 A | 11/2001 |
| WO | WO 9840337 A1 * | 9/1998 |

OTHER PUBLICATIONS

Moon et al., Journal of Polymer Science, Part A-1 (1970), 8(12), p. 3665-3666.

* cited by examiner

Primary Examiner—Bernard Dentz
(74) Attorney, Agent, or Firm—Birch, Stewart, Kolasch & Birch, LLP

(57) ABSTRACT

An adamantanetricarboxylic acid derivative is represented by following Formula (1):

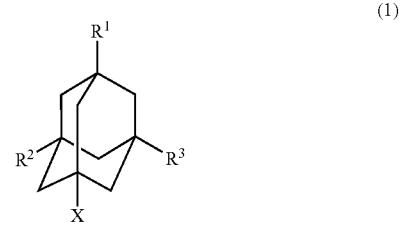

wherein X is a hydrogen atom or a hydrocarbon group; and $R^1$, $R^2$ and $R^3$ may be the same as or different from one another and are each a carboxyl group which may be protected by a protecting group, or a carbonyl halide group, wherein at least one of $R^1$, $R^2$ and $R^3$ is a carboxyl group which is protected by a protecting group, or a carbonyl halide group.

1 Claim, 1 Drawing Sheet

ADAMANTANETRICARBOXYLIC ACID DERIVATIVES

BACKGROUND OF THE INVENTION

This Nonprovisional application claims priority under 35 U.S.C. § 119(a) on Patent Application No(s). 2003-086166 filed in Japan on Mar. 26, 2003, the entire contents of which are hereby incorporated by reference.

1. Field of the Invention

The present invention relates to a novel adamantanetricarboxylic acid derivative which is useful for the formation of a film of a polybenzazole (imidazole, oxazole or thiazole) having high heat resistance and a low dielectric constant.

2. Description of the Related Art

Polybenzazoles having an adamantane skeleton are useful as highly heat resistant resins (Journal of Polymer Science, Part A-1 (1970), 8(12), p. 3665-3666). In particular, highly crosslinked polybenzazoles using a trifunctional adamantane derivative involve a multitude of molecular-scale voids, have a low relative dielectric constant and satisfactory mechanical strength and heat resistance and are thereby very useful as materials for interlayer dielectrics (Japanese Unexamined Patent Application Publication (JP-A) No. 2001-332543). These highly crosslinked polybenzazoles can be prepared, for example, by heating a material in the presence of a condensing agent such as a polyphosphoric acid. However, the resulting highly crosslinked resin is hardly soluble in solvent and cannot be significantly applied to a substrate by coating, thus a film having a sufficient thickness necessary as an interlayer dielectric cannot be significantly formed.

A thin film of a wholly aromatic chain polybenzazole is formed by a method in which an aldehyde derivative as a material monomer is spread over an aqueous solution of an amine as another material monomer to form a film by polymerization on a gas-liquid interface; the film is laminated on a substrate by a horizontal attachment method and is subjected to a thermal treatment in the air to form a thin film of a polybenzazole (Japanese Unexamined Patent Application Publication (JP-A) No. 62-183881). However, the method is not suitable for industrial production, since it takes quite a long time to form the thin film. In addition, the precursor polyimine is subjected to an oxidative thermal treatment in a final process, and the resulting polybenzazole film may be possibly oxidized, thus a lower dielectric constant as a dielectric film is not expected.

In addition, adamantanepolycarboxylic acid derivatives used as a material monomer have a significantly high polarity as a compound and are soluble in quite limited types of solvents. In particular, these monomers are hardly soluble in a solvent having a relatively low polarity, and a film having a thickness of several hundreds nanometers required as an interlayer dielectric for a semiconductor device cannot significantly be formed. Thus, dielectric films of highly crosslinked polybenzazoles using a trifunctional adamantane derivative have been hardly formed.

SUMMARY OF THE INVENTION

Accordingly, an object of the present invention is to provide a novel adamantanetricarboxylic acid derivative that can yield a polybenzazole having a high degree of crosslinking and is useful as a material which can easily form a dielectric film having a thickness required as an interlayer dielectric.

Another object of the present invention is to provide a novel adamantanetricarboxylic acid derivative useful for the formation of a dielectric film which contains a polybenzazole having high heat resistance and a low dielectric constant and is useful as semiconductor parts.

After intensive investigations to achieve the above objects, the present inventors have found that an adamantanetricarboxylic acid derivative, in which at least one of its three carboxyl groups is protected by a protecting group, has a significantly improved solubility in solvent; and by using this compound as a monomer component, a material composition for a dielectric film having a high monomer concentration can be prepared to thereby form a dielectric film having a thickness necessary as an interlayer dielectric. The present invention has been accomplished based on these findings.

Specifically, the present invention provides an adamantanetricarboxylic acid derivative represented by following Formula (1):

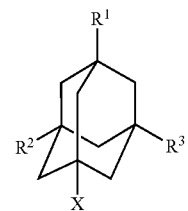

wherein X is a hydrogen atom or a hydrocarbon group; and $R^1$, $R^2$ and $R^3$ may be the same as or different from one another and are each a carboxyl group which may be protected by a protecting group, or a carbonyl halide group, wherein at least one of $R^1$, $R^2$ and $R^3$ is a carboxyl group which is protected by a protecting group, or a carbonyl halide group.

The adamantanetricarboxylic acid derivative has significantly improved solubility in solvent and, when used as a material for dielectric films, can form a dielectric film with a sufficient thickness which contains a highly crosslinked polybenzazole having an adamantane skeleton. The material can have increased solubility in various solvents to thereby yield polybenzazole films having thickness within a broad range corresponding to a variety of semiconductor fabrication processes. The resulting dielectric film formed from the material can exhibit high heat resistance and a low dielectric constant.

Further objects, features and advantages of the present invention will become apparent from the following description of the preferred embodiments with reference to the attached drawing.

DESCRIPTION OF THE PREFERRED EMBODIMENTS

Figure 1:
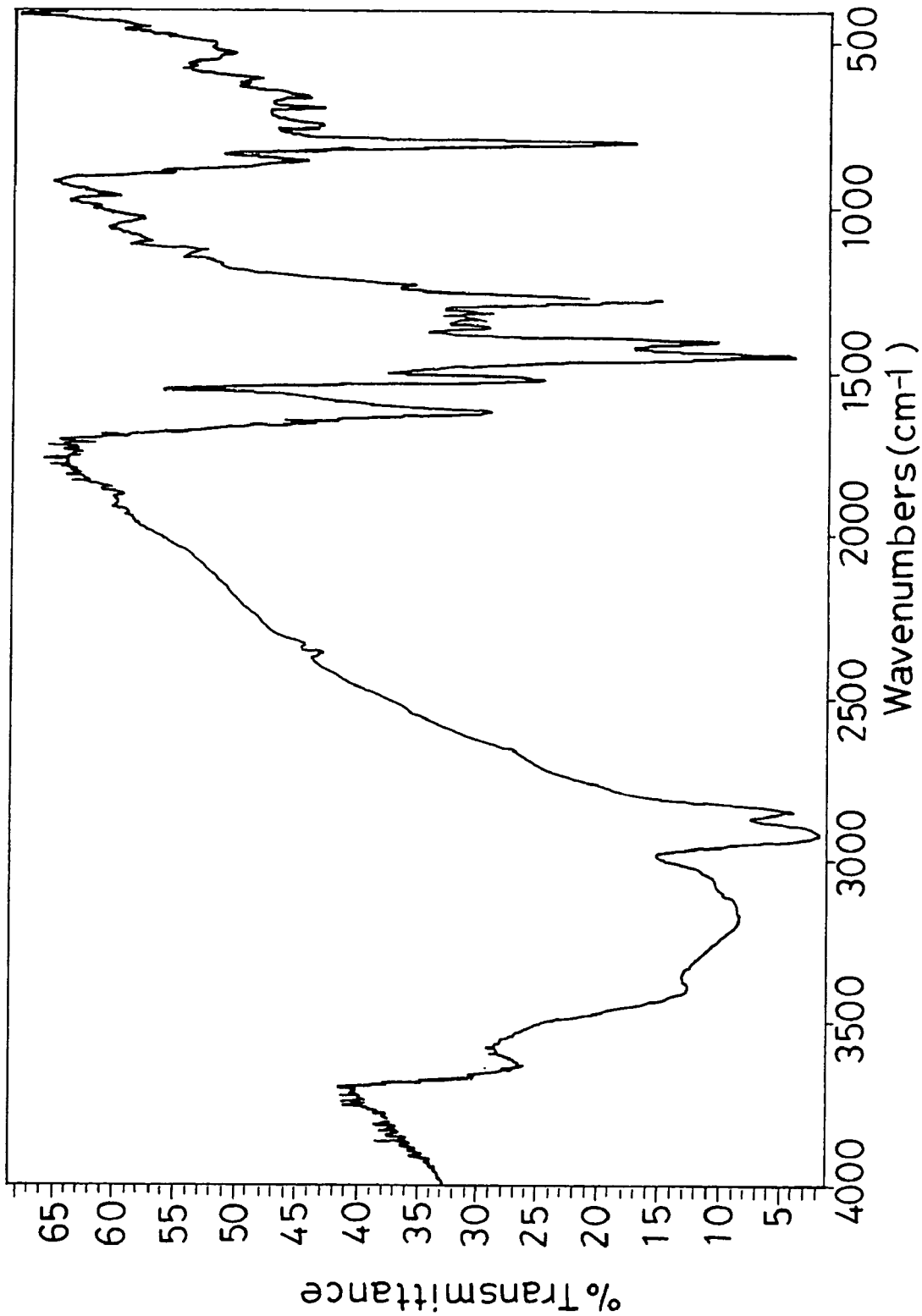
FIG. 1 shows an infrared absorption spectrum of a polymer film prepared in Example 7.

The adamantanetricarboxylic acid derivatives of the present invention are represented by Formula (1). In Formula (1), the hydrocarbon group in X includes, for example, aliphatic hydrocarbon groups, alicyclic hydrocarbon groups, aromatic hydrocarbon groups, and groups comprising two or more of these groups combined with each other. Examples of the aliphatic hydrocarbon groups are methyl, ethyl, propyl, isopropyl, butyl, isobutyl, s-butyl, t-butyl, pentyl, hexyl, decyl, dodecyl, and other straight- or branched-chain alkyl groups each having about 1 to about 20 carbon atoms, of which those having 1 to 10 carbon atoms are preferred, and those having 1 to 6 carbon atoms are more preferred; vinyl, allyl, 1-butenyl, 3-methyl-4-pentenyl, and other straight- or branched-chain alkenyl groups each having about 2 to about 20 carbon atoms, of which those having 2 to 10 carbon atoms are preferred, and those having 2 to 5 carbon atoms are more preferred; ethynyl, propynyl, 1-butynyl, 2-butynyl, and other straight- or branched-chain alkynyl groups each having about 2 to about 20 carbon atoms, of which those having 2 to 10 carbon atoms are preferred, and those having 2 to 5 carbon atoms are more preferred.

Examples of the alicyclic hydrocarbon groups are monocyclic alicyclic hydrocarbon groups, such as cyclopropyl, cyclobutyl, cyclopentyl, cyclohexyl, cyclooctyl, and other cycloalkyl groups each having about 3 to about 20 members, of which those having 3 to 15 members are preferred, and those having 3 to 12 members are more preferred; cyclopropenyl, cyclobutenyl, cyclopentenyl, cyclohexenyl, and other cycloalkenyl groups each having about 3 to about 20 members, of which those having 3 to 15 members are preferred, and those having 3 to 10 members are more preferred. Examples of the alicyclic hydrocarbon groups also include bridged hydrocarbon groups each having, for example, a bicyclic, tricyclic or tetracyclic hydrocarbon ring such as adamantane ring, perhydroindene ring, decalin ring, perhydrofluorene ring, perhydroanthracene ring, perhydrophenanthrene ring, tricyclo[5.2.1.0$^{2,6}$]decane ring, perhydroacenaphthene ring, perhydrophenalene ring, norbornane ring, and norbornene ring. Examples of the aromatic hydrocarbon groups are phenyl, naphthyl, and other aromatic hydrocarbon groups each having about 6 to about 20 carbon atoms, of which those having 6 to 14 carbon atoms are preferred.

Examples of hydrocarbon groups comprising an aliphatic hydrocarbon group and an alicyclic hydrocarbon group combined with each other include cyclopentylmethyl, cyclohexylmethyl, 2-cyclohexylethyl, other $C_3$–$C_{20}$ cycloalkyl-$C_1$–$C_4$ alkyl groups, and other cycloalkyl-alkyl groups. Examples of hydrocarbon groups comprising an aliphatic hydrocarbon group and an aromatic hydrocarbon group combined with each other include $C_7$–$C_{18}$ aralkyl groups, and other aralkyl groups; and phenyl or naphthyl group substituted with about one to about four $C_1$–$C_4$ alkyl groups, and other alkyl-substituted aryl groups.

These aliphatic hydrocarbon groups, alicyclic hydrocarbon groups, aromatic hydrocarbon groups, and groups comprising these groups combined with each other may each have one or more substituents. Such substituents are not specifically limited, as long as they do not adversely affect the reaction and examples thereof include halogen atoms such as fluorine, chlorine, bromine and iodine atoms; substituted oxy groups including alkoxy groups such as methoxy and ethoxy groups, cycloalkyloxy groups, aryloxy groups, acyloxy groups, and silyloxy groups; substituted oxycarbonyl groups such as alkyloxycarbonyl groups and aryloxycarbonyl groups; acyl groups including aliphatic acyl groups such as acetyl group, acetoacetyl group, alicyclic acyl groups, and aromatic acyl groups; aliphatic hydrocarbon groups; alicyclic hydrocarbon groups; aromatic hydrocarbon groups; and heterocyclic groups.

The substituent X is preferably a hydrogen atom, a $C_1$–$C_6$ alkyl group or a $C_6$–$C_{14}$ aromatic hydrocarbon group.

Examples of the carboxyl-protecting group in $R^1$, $R^2$ and $R^3$ in Formula (1) are alkoxy groups including, for example, $C_1$–$C_{10}$ alkoxy groups such as methoxy, ethoxy, propoxy, isopropoxy, butoxy, isobutoxy, s-butoxy, t-butoxy and hexyloxy groups, and ($C_1$–$C_4$ alkoxy)$_{1-2}$-$C_1$–$C_4$ alkoxy groups such as methoxymethyloxy and methoxyethoxymethyloxy groups; cycloalkyloxy groups including, for example, $C_3$–$C_{20}$ cycloalkyloxy groups such as cyclopentyloxy and cyclohexyloxy groups; tetrahydrofuranyloxy group; tetrahydropyranyloxy group; aryloxy groups including, for example, $C_6$–$C_{20}$ aryloxy groups such as phenoxy and methylphenoxy groups; aralkyloxy groups including, for example, $C_7$–$C_{18}$ aralkyloxy groups such as benzyloxy and diphenylmethyloxy groups; trialkylsilyloxy groups including, for example, tri-$C_1$–$C_4$ alkyl-silyloxy groups such as trimethylsilyloxy and triethyllsilyloxy groups; amino groups which may have one or more substituents including, for example, amino group, mono- or di-substituted $C_1$–$C_6$ alkylamino groups such as methylamino, dimethylamino, ethylamino and diethylamino groups, and cyclic amino groups such as pyrrolidino and piperidino groups; hydrazino groups which may have one or more substituents, including, for example, hydrazino group, N-phenylhydrazino group, alkoxycarbonylhydrazino groups including $C_1$–$C_{10}$ alkoxycarbonylhydrazino groups such as t-butoxycarbonylhydrazino group, aralkyloxycarbonylhydrazino group including $C_7$–$C_{18}$ aralkyloxycarbonylhydrazino groups such as benzyloxycarbonylhydrazino group; and acyloxy groups including, for example, $C_1$–$C_{10}$ acyloxy groups such as acetoxy and propionyloxy groups. The carbonyl-protecting group is not limited to the above examples, and other protecting groups conventionally used in the field of organic synthesis can also be used.

Examples of the carbonyl halide groups (haloformyl groups) are carbonyl chloride group, carbonyl bromide group, carbonyl fluoride group, and carbonyl iodide group.

The compounds represented by Formula (1) are adamantanetricarboxylic acid mono-, di- or tri-esters when $R^1$, $R^2$ and/or $R^3$ is, for example, an alkoxy group or aryloxy group; they are adamantanetricarboxylic mono-, di- or tri-amides when $R^1$, $R^2$ and/or $R^3$ is an amino group which may have a substituent; and they are adamantanetricarboxylic acid mono-, di- or tri-halides when $R^1$, $R^2$ and/or $R^3$ is a carbonyl halide group.

Preferred examples of $R^1$, $R^2$ and $R^3$ are carboxyl group, $C_1$–$C_6$ alkoxy-carbonyl groups, ($C_1$–$C_4$ alkoxy)$_{1-2}$-$C_1$–$C_4$ alkoxy-carbonyl groups, N-substituted carbamoyl groups, tetrahydropyranyloxycarbonyl group, tetrahydrofuranyloxycarbonyl group, aryloxycarbonyl groups, trialkylsilyloxycarbonyl groups, and carbonyl halide groups.

The adamantanetricarboxylic acid derivatives in the present invention include compounds, in which one of the three functional groups (carboxyl groups or equivalent groups thereof) is a carboxyl group protected by a protecting group (hereinafter briefly referred to as "protected carboxyl group") or a carbonyl halide group; compounds, in which two of the functional groups are each a protected carboxyl group or a carbonyl halide group; and compounds, in which the three functional groups are each a protected carboxyl group or a carbonyl halide group.

Typical examples of the adamantanetricarboxylic acid derivatives, in which one of the three functional groups is a protected carboxyl group or a carbonyl halide group, are 1-methoxycarbonyl-3,5-adamantanedicarboxylic acid, 1-(t-butoxycarbonyl)-3,5-adamantanedicarboxylic acid, 1-tetrahydropyranyl(THP)oxycarbonyl-3,5-adamantanedicarboxylic acid, 1-phenoxycarbonyl-3,5-adamantanedicarboxylic acid, 1-methoxymethyl(MEM)oxycarbonyl-3,5-adamantanedicarboxylic acid, 1-trimethylsilyl (TMS)oxycarbonyl-3,5-adamantanedicarboxylic acid, 1,3-dicarboxy-5-adamantanecarbonyl chloride, 1-diethylcarbamoyl-3,5-adamantanedicarboxylic acid, 1-pyrrolidinylcarbonyl-3,5-adamantanedicarboxylic acid, and 1,3-bis(4-carboxyphenyl)-5-(4-metoxycarbonylphenyl) adamantane.

Typical examples of the adamantanetricarboxylic acid derivatives, in which two of the three functional groups are each a protected carbonyl group or a carbonyl halide group, are 1,3-bis(methoxycarbonyl)-5-adamantanemonocarboxylic acid, 1,3-bis(t-butoxycarbonyl)-5-adamantanemonocarboxylic acid, 1,3-bis(tetrahydropyranyl(THP)oxycarbonyl)-5-adamantanemonocarboxylic acid, 1,3-bis(phenoxycarbonyl)-5-adamantanemonocarboxylic acid, 1,3-bis(methoxymethyl(MEM)oxycarbonyl)-5-adamantanemonocarboxylic acid, 1,3-bis(trimethylsilyl (TMS)oxycarbonyl)-5-adamantanemonocarboxylic acid, 1-carboxy-3,5-adamantanedicarbonyldichloride, 1,3-bis(diethylcarbamoyl)-5-adamantanemonocarboxylic acid, 1,3-bis(1-pyrrolidinylcarbonyl)-5-adamantanemonocarboxylic acid, and 1-(4-carboxyphenyl)-3,5-bis(4-methoxycarbonylphenyl)-adamantane.

Typical examples of adamantanetricarboxylic acid derivatives, in which all the three functional groups are each a protected carboxyl group or a carbonyl halide group, are 1,3,5-tris(methoxycarbonyl)adamantane, 1,3,5-tris(t-butoxycarbonyl)adamantane, 1,3,5-tris(tetrahydropyranyl(THP)oxycarbonyl)adamantane, 1,3,5-tris(phenoxycarbonyl)adamantane, 1,3,5-tris(methoxymethyl(MEM)oxycarbonyl)adamantane, 1,3,5-tris(trimethylsilyl(TMS)oxycarbonyl)adamantane, 1,3,5-adamantanetricarbonyl trichloride, 1,3,5-tris(diethylcarbamoyl)adamantane, 1,3,5-tris(1-pyrrolidinylcarbonyl)adamantane, and 1,3,5-tris(4-methoxycarbonylphenyl)adamantane.

Each of these adamantanetricarboxylic acid derivatives can be used alone or in combination for use as, for example, a material for dielectric films.

The adamantanetricarboxylic acid derivative represented by Formula (1) can be prepared by introducing a desired protecting group into a material adamantanetricarboxylic acid (a corresponding compound of Formula (1), except that all $R^1$, $R^2$ and $R^3$ are carboxyl groups) according to a conventional reaction for introducing a protecting group. The material adamantanetricarboxylic acid can be prepared according to a conventional procedure.

Of the adamantanetricarboxylic acid derivatives represented by Formula (1), adamantanetricarboxylic acid esters can be prepared according to a conventional method for producing carboxylic acid esters using a carboxylic acid as a raw material, described in, for example, "Experimental Chemistry, New Ed., 14, Syntheses and Reactions of Organic Compounds II" (Maruzen Co., Ltd., Tokyo) or "Protective Groups in Organic Synthesis" (John Wiley & Sons, Inc. NJ). To prepare adamantanecarboxylic acid esters, for example, (i) a reaction between an adamantanetricarboxylic acid and an alcohol, (ii) a reaction between an adamantanetricarboxylic acid and an alcohol ester, (iii) a reaction between an adamantanetricarboxylic acid and an alkene or alkyne, (iv) a reaction between an adamantanetricarboxylic acid and an o-alkylating agent, or (v) a reaction between adamantanetricarboxylic acid halide and an alcohol can be used.

Using the reaction (i) between an adamantanetricarboxylic acid and an alcohol, a target adamantanetricarboxylic acid ester can be prepared, for example, by dehydrating an adamantanetricarboxylic acid and a corresponding alcohol or phenol at room temperature or at an elevated temperature. This reaction can be performed in the presence of an acid catalyst. Examples of the acid catalyst are sulfuric acid, hydrochloric acid, and other inorganic acids; p-toluenesulfonic acid, methanesulfonic acid, and other organic acids; boron fluoride-ether complex, and other Lewis acids; acidic ion-exchange resins, and other resins. The material compounds can be dehydrated, for example, by separating water with a Dean-Stark water separator using a solvent such as toluene; by refluxing a solvent in a Soxhlet extractor containing a desiccating agent such as anhydrous magnesium sulfate or a molecular sieve; or adding a desiccating agent such as dicyclohexylcarbodiimide (DCC) to the reaction system.

Using the reaction (ii) between an adamantanetricarboxylic acid and an alcohol ester, a target adamantanetricarboxylic acid ester can be prepared, for example, by transesterifying an adamantanetricarboxylic acid and a corresponding alcohol ester at room temperature or at an elevated temperature. This reaction can be performed in the presence of an acid catalyst and/or a transesterification catalyst. Those exemplified as the acid catalyst in the reaction (i) can be used herein. A by-produced carboxylic acid can be removed, for example, by refluxing a solvent in the presence of, for example, a molecular sieve using a Dean-Stark water separator or a Soxhlet extractor.

Using the reaction (iii) between an adamantanetricarboxylic acid and an alkene or alkyne, a target adamantanetricarboxylic acid ester can be prepared, for example, by reacting an adamantanetricarboxylic acid with the alkene or alkyne at room temperature or at an elevated temperature in the presence of an acid catalyst. Those exemplified as the acid catalyst in the reaction (i) can be used herein. For example, by using isobutene as the alkene, t-butyl ester of adamantanetricarboxylic acid can be easily prepared. Likewise, by using dihydropyran, tetrahydropyranyl ester of adamantanetricarboxylic acid can be easily prepared.

Using the reaction (iv) between an adamantanetricarboxylic acid and an O-alkylating agent, a target adamantanetricarboxylic acid ester can be prepared, for example, by reacting the adamantanetricarboxylic acid and a corresponding O-alkylating agent at room temperature or at an elevated temperature. For example, by using diazomethane as the O-alkylating agent, methyl ester of adamantanetricarboxylic acid can be easily prepared. Likewise, by using a methoxyethoxymethyl halide, methoxyethoxymethyl ester of adamantanetricarboxylic acid can be easily prepared.

Using the reaction (v) between an adamantanetricarboxylic acid halide and an alcohol, a target adamantanetricarboxylic acid ester can be prepared, for example, by reacting an adamantanetricarboxylic acid halide and an alcohol at room temperature or at an elevated temperature. A base such as pyridine or triethylamine can be incorporated in the reaction system to trap a generated hydrogen halide. An alkoxide prepared by reacting an alcohol with, for example, sodium or an alkyllithium can also be used as the alcohol. The adamantanetricarboxylic acid halide can be prepared, for example, halogenating a corresponding adamantanetricarboxylic acid with thionyl chloride, phosgene, phosphorus trichloride or benzoyl chloride. By using the reaction (v), adamantanetricarboxylic acid derivatives which are unstable against acids, such as t-butyl ester of adamantanetricarboxylic acid, can be easily prepared.

The adamantanecarboxylic amides can be prepared according to a conventional method for producing carboxylic amides using a carboxylic acid as a raw material, described in, for example, "Experimental Chemistry, New Ed., 14, Syntheses and Reactions of Organic Compounds II" (Maruzen Co., Ltd., Tokyo) or "Protective Groups in Organic Synthesis" (John Wiley & Sons, Inc. N.J.). More specifically, the adamantanetricarboxylic amides can-be prepared, for example, by using a reaction between an adamantanetricarboxylic acid and an amine or ammonia, or a reaction between an adamantanetricarboxylic acid halide and an amine.

Using the reaction between an adamantanetricarboxylic acid and an amine or ammonia, a target adamantanetricarboxylic amide can be prepared, for example, by dehydrating an adamantanetricarboxylic acid and a corresponding amine or ammonia at room temperature or at an elevated temperature. The dehydration can be performed according to the dehydration procedures exemplified in the reaction (i).

Using the reaction between an adamantanetricarboxylic acid halide and an amine, a target adamantanetricarboxylic amide can be prepared, for example, by reacting an adamantanetricarboxylic acid halide and an amine at room temperature or at an elevated temperature. A generated hydrogen halide may be trapped by incorporating a base such as pyridine or triethylamine into the reaction system or by using the material amine in excess. Lithium amide which has been prepared by reacting an amine with, for example, an alkyllithium can also be used as the amine. The Schotten-Baumann method, in which an acid halide is added dropwise to a mixture of an amine and an alkaline aqueous solution, or a method in which the reaction is performed in a dual-layer system comprising an organic solvent and water, can be employed. The adamantanetricarboxylic acid halide can be prepared according to the procedure described in the reaction (v).

The adamantanetricarboxylic acid derivatives of the present invention are useful as materials for dielectric films which contain a polybenzazole with high heat resistance and a low dielectric constant and are useful as, for example, semiconductor parts.

The dielectric film comprising a polybenzazole may be formed by applying a material polymerizable composition to a substrate, and heating the applied film for polymerization. The material polymerizable composition is prepared by dissolving the adamantanetricarboxylic acid derivative and an aromatic polyamine or a derivative thereof in an organic solvent.

Examples of the aromatic polyamine or a derivative thereof include a compound represented by following Formula (2) or (2a):

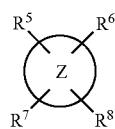

(2)

wherein Ring Z is a monocyclic or polycyclic aromatic ring; $R^5$, $R^6$, $R^7$ and $R^8$ are each a substituent bound to Ring Z; $R^5$ and $R^6$ may be the same as or different from each other and are each an amino group which may be protected by a protecting group; and $R^7$ and $R^8$ may be the same as or different from each other and are each an amino group which may be protected by a protecting group, a hydroxyl group which may be protected by a protecting group or a mercapto group which may be protected by a protecting group, wherein when $R^5$ and $R^6$ are both amino groups, at least one of $R^7$ and $R^8$ is an amino group protected by a protecting group, a hydroxyl group protected by a protecting group or a mercapto group protected by a protecting group;

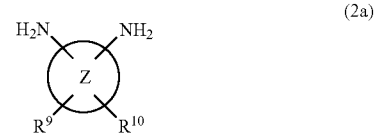

(2a)

wherein Ring Z is a monocyclic or polycyclic aromatic ring; $R^9$ and $R^{10}$ are each a substituent bound to Ring Z, may be the same as or different from each other and are each an amino group, a hydroxyl group or a mercapto group.

The aromatic ring in Ring Z includes monocyclic or polycyclic aromatic hydrocarbon rings and aromatic heterocyclic rings. An example of the monocyclic aromatic hydrocarbon rings is benzene ring. Examples of the polycyclic hydrocarbon rings are naphthalene ring, anthracene ring, phenanthrene ring, phenalene ring, and other rings having a fused structure in which two or more aromatic rings commonly possess two or more atoms; and biphenyl ring, biphenylene ring, fluorene ring, and other rings having a structure in which two or more aromatic rings are bound via a linkage group such as a single bond, or an alicyclic ring. Examples of the aromatic heterocyclic rings are monocyclic or polycyclic aromatic heterocyclic rings containing one or more hetero atoms such as oxygen atom, sulfur atom and nitrogen atom. Specific examples of the aromatic heterocyclic rings are furan ring, thiophene ring, pyridine ring, picoline ring, and other monocycles; quinoline ring, isoquinoline ring, acridine ring, phenazine ring, and other polycycles. Each of these aromatic rings may have one or more substituents. Such substituents are not specifically limited, as long as they do not adversely affect the reaction.

Examples of the amino-protecting group in $R^5$ and $R^6$ in Formula (2) are acyl groups including $C_1$–$C_6$ aliphatic acyl groups such as acetyl group, and aromatic acyl group having about 6 to about 20 carbon atoms, such as benzoyl and naphthoyl groups; alkoxycarbonyl groups including $C_1$–$C_4$ alkoxy-carbonyl groups such as methoxycarbonyl, ethoxycarbonyl and t-butoxycarbonyl groups; aralkyloxycarbonyl groups including $C_7$–$C_{20}$ aralkyloxy-carbonyl groups such as benzyloxycarbonyl group; and alkylidene groups including $C_1$–$C_{10}$ aliphatic alkylidene groups such as methylidene, ethylidene, propylidene, isopropylidene, cyclopentylidene, hexylidene and cyclohexylidene groups, and $C_6$–$C_{20}$ aromatic alkylidene groups such as benzylidene and methylphenylmethylidene groups.

The protected amino groups include mono-substituted amino groups, as long as they do not adversely affect the reaction for the formation of polybenzazole. Examples of such mono-substituted amino groups are methylamino group, ethylamino group, propylamino group, butylamino group, t-butylamino group, and other alkylamino groups; cyclohexylamino group and other cycloalkylamino groups; phenylamino group and other arylamino groups; benzylamino group and other aralkylamino groups. The amino-protecting group is not limited to the above examples, and other protecting groups conventionally used in the field of organic synthesis can also be used.

The amino-protecting group in $R^7$, $R^8$, $R^9$ and $R^{10}$ can be any of those exemplified as the amino-protecting group in $R^5$ and $R^6$. A protecting group that can protect plural amino groups concurrently (polyfunctional protecting group) can also be used as the amino-protecting group. Examples of such polyfunctional protecting groups are carbonyl group, oxalyl group and butane-2,3-diylidene group. By using such a polyfunctional protecting group to protect two of $R^5$, $R^6$, $R^7$ and $R^8$ concurrently, a ring adjacent to Ring Z is formed. Examples of the hydroxyl-protecting group are alkyl groups including $C_1$–$C_6$ alkyl groups such as methyl and ethyl groups; cycloalkyl groups including 3- to 15-membered cycloalkyl groups such as cyclopentyl and cyclohexyl groups; aralkyl groups including $C_7$–$C_{18}$ aralkyl groups such as benzyl group; substituted methyl groups including substituted methyl groups each having a total of about 2 to about 10 carbon atoms, such as methoxymethyl, benzyloxymethyl and t-butoxymethyl groups; substituted ethyl groups such as 1-ethoxyethyl and 1-methyl-1-methoxyethyl groups; acyl groups including $C_1$–$C_6$ aliphatic acyl groups such as acetyl group, $C_4$–$C_{20}$ alicyclic acyl groups such as cyclohexylcarbonyl group, and $C_7$–$C_{20}$ aromatic acyl groups such as benzoyl and naphthoyl groups; alkoxycarbonyl groups including $C_1$–$C_4$ alkoxy-carbonyl groups such as methoxycarbonyl and ethoxycarbonyl groups; aralkyloxycarbonyl groups including $C_7$–$C_{20}$ aralkyloxy-carbonyl groups such as benzyloxycarbonyl and p-methoxybenzyloxycarbonyl groups. The mercapto-protecting group can be any of groups exemplified as the hydroxyl-protecting group.

The substituents $R^7$ and $R^8$ in Ring Z in Formula (2) are preferably positioned at the alpha-position or the beta-position with respect to carbon atoms in Ring Z having $R^5$ and $R^6$, e.g., amino groups which may be protected by a protecting group, respectively. Likewise, the substituents $R^9$ and $R^{10}$ in Ring Z in Formula (2a) are preferably positioned at the alpha-position or the beta-position with respect to carbon atoms in Ring Z having, e.g., —$NH_2$ (amino group), respectively.

For example, by reacting an aromatic polyamine having $R^7$ ($R^8$) at the alpha-position to a carbon atom having $R^5$ ($R^6$) in Ring Z in Formula (2) [or having $R^9$ ($R^{10}$) at the alpha-position to a carbon atom having —$NH_2$ in Ring Z in Formula (2a)] or a derivative thereof with the adamantanetricarboxylic acid or a derivative thereof, the amino- and/or carboxyl-protecting group is generally removed to form a 5-membered azole ring. For example, an imidazole ring is formed when $R^7$ is an amino group which may be protected by a protecting group; an oxazole ring is formed when $R^7$ is a hydroxyl group which may be protected by a protecting group; and a thiazole ring is formed when $R^7$ is a mercapto group which may be protected by a protecting group.

By reacting an aromatic polyamine having $R^7$ ($R^8$) at the beta-position to a carbon atom having $R^5$ ($R^6$) in Ring Z in Formula (2) [or having $R^9$ ($R^{10}$) at the beta-position to a carbon atom having —$NH_2$ in Ring Z in Formula (2a)] or a derivative thereof with the adamantanetricarboxylic acid or a derivative thereof, the amino- and/or carboxyl-protecting group is generally removed to form a 6-membered nitrogen-containing ring. For example, a hydrodiazine ring is formed when $R^7$ ($R^9$) is an amino group or mono-substituted amino group; an oxazine ring is formed when $R^7$ ($R^9$) is a hydroxyl group; and a thiazine ring is formed when $R^7$ ($R^9$) is a mercapto group.

The positions of $R^5$ and $R^6$ in Ring Z in Formula (2), and those of the amino groups in Ring Z in Formula (2a) are not specifically limited, as long as these groups can be combined with carboxyl groups in the adamantanetricarboxylic acid to form, for example, a 5- or 6-membered ring together with adjacent carbon atoms, and are preferably such positions that $R^5$ and $R^6$ or the two amino groups are not adjacent to each other.

Typical examples of the aromatic polyamine derivative are, by taking a compound wherein Ring Z is a benzene ring as an example,
N,N',N'',N'''-tetracyclohexylidene-1,2,4,5-benzenetetramine, e, N,N',N'',N'''-tetraisopropylidene-1,2,4,5-benzenetetramine, N,N'-diisopropylidene-1,2,4,5-benzenetetramine, N-isopropylidene-1,2,4,5-benzenetetramine, 1,2,4,5-tetrakis(acetamino)benzene, 1,4-bis(acetamino)-2,5-diacetoxybenzene, N,N'-diisopropylidene-2,5-dihydroxy-1,4-benzenediamine, and other compounds represented by Formula (2); and 1,2,4,5-tetraaminobenzene, 1,4-diamino-2,5-dihydroxybenzene, 1,4-diamino-2,5-dimercaptobenzene, and other compound represented by Formula (2a).

Each of these aromatic polyamines can be used alone or in combination.

The aromatic polyamines and derivatives thereof represented by Formula (2) or (2a) can be prepared according to a conventional procedure or using a known organic synthesis reaction.

The material composition for dielectric films may further comprise other components in addition to the above components. For example, small amounts of other components can be added to the material composition. Examples of such other components are catalysts for accelerating the polymerization reaction, such as sulfuric acid and other acid catalysts; thickening agents (bodying agents) for increasing the viscosity of the composition, such as ethylene glycol; monocarboxylic acids for adjusting the molecular weight of the resulting polymer, such as adamantanecarboxylic acid; dicarboxylic acids for adjusting the degree of crosslinking after polymerization, such as adamantanedicarboxylic acid; adhesion promoters for increasing the adhesion of the resulting dielectric film to a substrate, such as trimethoxyvinylsilane.

Solvents for use herein are not specifically limited, as long as they do not adversely affect the cyclization reaction between the adamantanetricarboxylic acid derivative and the aromatic polyamine. Examples of such solvents are aliphatic hydrocarbons such as hexane, heptane and octane; alicyclic hydrocarbons such as cyclohexane and methylcyclohexane; aromatic hydrocarbons such as benzene, toluene, xylene, ethylbenzene and mesitylene; halogenated hydrocarbons such as dichloromethane, dichloroethane, chloroform and carbon tetrachloride; alcohols such as methanol, ethanol, propanol, butanol and ethylene glycol; ethers such as dioxane, tetrahydrofuran, diethyl ether and propylene glycol monomethyl ether (PGME); esters such as formic esters, acetic esters, propionic esters, benzoic esters, γ-butyrolactone and propylene glycol monomethyl ether acetate (PGMEA); ketones such as acetone, methyl ethyl ketone, diethyl ketone, methyl isobutyl ketone, cyclopentanone and cyclohexanone; carboxylic acids such as formic acid, acetic acid, propionic acid and butyric acid; aprotic polar solvents including nitriles such as acetonitrile, propionitrile and benzonitrile, amides such as formamide, dimethylformamide, acetamide, dimethylacetamide and N-methylpyrrolidone, and sulfoxides such as dimethyl sulfoxide. Each of these solvents can be used alone or in combination.

The polymerizable composition as the material composition for dielectric films can be prepared according to any procedure, as long as the adamantanetricarboxylic acid derivative and the aromatic polyamine (monomer components) can be completely dissolved in a solvent. For example, it can be prepared by stirring or leaving stand a mixture comprising the monomer components, solvent, and other components. The ratio of the adamantanetricarboxylic acid derivative to the aromatic polyamine can be set freely depending on the solubility in the solvent used, as long as the functions of the resulting dielectric film are not adversely affected. The molar ratio of the adamantanetricarboxylic acid derivative to the aromatic polyamine is preferably from about 10:90 to about 60:40, and more preferably from about 20:80 to about 50:50.

The total monomer amount of the adamantanetricarboxylic acid derivative and the aromatic polyamine can be arbitrarily set depending on the solubility in the solvent and is, for example, from about 5% by weight to about 70% by weight, and preferably from about 10% by weight to about 60% by weight relative to the amount of the solvent. The adamantanetricarboxylic acid derivative has a high solubility in solvent, and the material composition can contain the adamantanetricarboxylic acid derivative in a high concentration. A dielectric film formed from the material composition containing the monomer components in high concentrations can have an increased thickness, have excellent electric properties and have such a thickness that can support various semiconductor fabrication processes.

The components may be dissolved in the solvent in any atmosphere such as air atmosphere, as long as the aromatic polyamine is not oxidized, but preferably in an atmosphere of inert gas such as nitrogen or argon gas. The temperature for dissolution is not specifically limited and, where necessary, the composition may be heated depending on the solubility of the monomer components and the boiling point of the solvent. The temperature for dissolution is, for example, from about 0° C. to 200° C., and preferably from about 10° C. to about 150° C.

To form a dielectric film exhibiting high heat resistance due to its high degree of crosslinking, a possible material is a polycondensed product (polybenzazole) of an adamantanetricarboxylic acid derivative and an aromatic polyamine. However, such a polycondensed polybenzazole is highly crosslinked, thereby has a low solubility in solvent and cannot be significantly used as a material for forming a thin dielectric film by coating. In contrast, the material composition containing the adamantanetricarboxylic acid derivative and other monomer components completely dissolved in the solvent can be applied to a substrate as intact as a coating liquid. The applied film can be polymerized to thereby easily form a dielectric film comprising a highly crosslinked polybenzazole.

Examples of the substrate to which the material composition is applied are silicon wafers, metal substrates, and ceramic substrates. The material composition can be applied according to a conventional procedure not specifically limited, such as spin coating, dip coating or spray coating.

The heating can be performed at any temperature, as long as the polymerizable components can be polymerized, and is performed at a temperature, for example, from about 100° C. to about 500° C., and preferably from about 150° C. to about 450° C. at a constant temperature or with a stepwise temperature gradient. The heating can be performed in any atmosphere such as air atmosphere, as long as the properties of the resulting thin film are not adversely affected, but preferably in an atmosphere of inert gas such as nitrogen or argon gas, or in vacuo.

As a result of heating, the polycondensation reaction between the adamantanetricarboxylic acid derivative and the aromatic polyamine in the material composition proceeds to form an adamantane-skeleton-containing polybenzazole (an imidazole, an oxazole or a thiazole) as a polymerized product.

The dielectric film formed from the material composition by heating is a polymer containing adamantane ring, aromatic ring, and azole ring or 6-membered nitrogen-containing ring (a ring formed in a polycondensed moiety) as main constitutional units. The dielectric film is formed from the adamantanetricarboxylic acid having three functional groups and is a highly crosslinked polymer film, in which the adamantane compound having a three-dimensional structure and the aromatic polyamine having a two-dimensional structure are combined to form a structure having crosslinks in three directions with the adamantane skeleton as a vertex (crosslinking point). That is, the film has a unit in which three hexagons commonly possess two vertexes or two sides. The dielectric film involves a multitude of uniformly dispersed molecular-scale voids and can have a satisfactorily low relative dielectric constant.

The thickness of the dielectric film formed by heating is, for example, about 50 nm or more (e.g., from about 50 to about 2000 nm), preferably about 100 nm or more (e.g., from about 100 to about 2000 nm), and more preferably about 300 nm or more (e.g., from about 300 to about 2000 nm). Using the material composition, a coating liquid containing the monomer components in high concentrations can be prepared to thereby form a film having the aforementioned thickness even it is a dielectric film comprising a polybenzazole. If the thickness is less than about 50 nm, leak current may occur, electric properties may be adversely affected, or the resulting film may not be satisfactorily smoothened by chemical-mechanical polishing (CMP) in a semiconductor fabrication process. Accordingly, such a film having an excessively small thickness is not suitable as an interlayer dielectric.

The dielectric film can have a low dielectric constant and high heat resistance. It can be used, for example, as a dielectric coating in electronic material parts such as semiconductor devices and is particularly useful as an interlayer dielectric.

The present invention will be illustrated in further detail with reference to several examples and comparative examples below, which are not intended to limit the scope of the invention. The symbols "s", "m" and "w" in infrared absorption spectral data mean absorption intensity of a wavelength indicated prior to each symbol, and means that the absorption is "strong", "medium" or "weak", respectively. The thickness of the polymer film was determined with an ellipsometer.

PREPARATION EXAMPLE 1

Preparation of 3,3'-diaminobenzidinetetracyclohexanoimine [N,N',N'',N'''-tetracyclohexylidene-3,4,3',4'-biphenyltetramine]

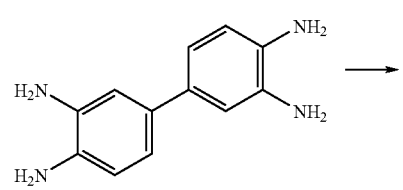

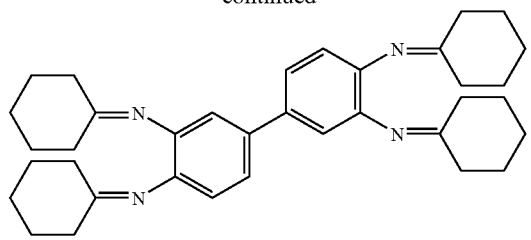

In a 200-ml flask equipped with a stirrer, a condenser and a thermometer were placed 21.4 g (100 mmol) of 3,3'-diaminobenzidine and 100 ml of cyclohexanone, followed by heating at 60° C. in a nitrogen atmosphere with stirring for 2 hours. After cooling to room temperature, cyclohexanone was removed under reduced pressure. The residue was purified by silica gel chromatography, to yield 48.1 g (90 mmol) of the target 3,3'-diaminobenzidinetetracyclohexanoimine[N,N',N'',N'''-tetracyclohexylidene-3,4,3',4'-biphenyltetramine] in a yield of 90%.

Infrared absorption spectral data (cm$^{-1}$): 1636 (C=N) MS: 535 (M+H), 491, 453

EXAMPLE 1

Preparation of Trimethyl Ester of 1,3,5-adamantanetricarboxylic acid

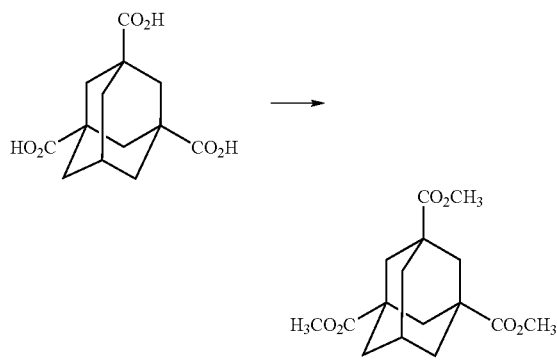

In a 200-ml flask equipped with a stirrer, a condenser and a thermometer were placed 26.8 g (100 mmol) of 1,3,5-adamantanetricarboxylic acid, 100 ml of methanol and 0.49 g (5 mmol) of sulfuric acid, followed by heating under reflux in a nitrogen atmosphere for 3 hours. After cooling to room temperature, methanol was removed under reduced pressure. The reaction mixture was dissolved in ethyl acetate, and the ethyl acetate solution was washed with 10% aqueous sodium carbonate solution and water to remove a residual acid component, followed by removal of ethyl acetate under reduced pressure therefrom, to yield 27.3 g (88 mmol) of trimethyl ester of 1,3,5-adamantanetricarboxylic acid in a yield of 88%.

[NMR Spectral Data] $^1$H-NMR (CDCl$_3$) δ (ppm): 1.84 (m, 6H), 2.01 (m, 6H), 2.30 (m, 1H), 3.65 (m, 9H) $^{13}$C-NMR (CDCl$_3$) δ (ppm): 27.86, 37.06, 39.11, 41.28, 51.91, 176.40

EXAMPLE 2

Preparation of 1,3,5-adamantanetricarbonyl trichloride

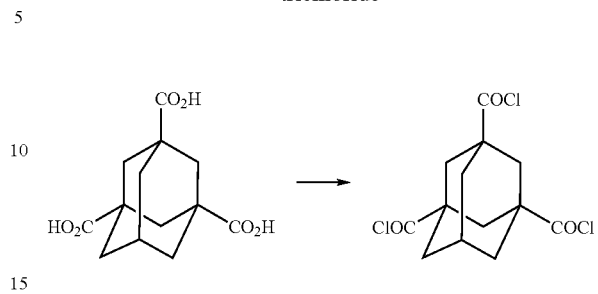

In a 200-ml flask equipped with a stirrer, a condenser, a thermometer and an acidic gas trap were placed and stirred 26.8 g (100 mmol) of 1,3,5-adamantanetricarboxylic acid and 59.5 g (500 mmol) of thionyl chloride. To the mixture was added dropwise 0.37 g (5 mmol) of dimethylformamide (DMF) at room temperature, and the mixture was gradually heated in a nitrogen atmosphere, followed by stirring at 70° C. for 3 hours. After cooling to room temperature, the residual thionyl chloride and DMF were removed under reduced pressure, to yield 31.4 g (97 mmol) of 1,3,5-adamantanetricarbonyl trichloride in a yield of 97%.

[NMR Spectral Data] $^1$H-NMR (CDCl$_3$) δ (ppm): 1.74 (m, 6H), 1.95 (m, 6H), 2.33 (m, 1H) $^{13}$C-NMR (CDCl$_3$) δ (ppm): 27.70, 36.52, 39.89, 51.21, 178.63

EXAMPLE 3

Preparation of Tri-tert-butyl ester of 1,3,5-adamantanetricarboxylic acid

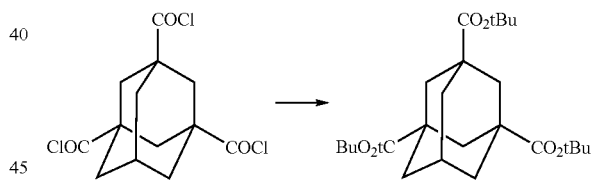

In a 500-ml flask equipped with a stirrer, a thermometer and a dropping funnel were placed 32.6 g (340 mmol) of sodium tert-butoxide and 140 ml of toluene. To the stirred mixture under ice-cooling in a nitrogen atmosphere, 31.4 g (97 mmol) of 1,3,5-adamantanetricarbonyl trichloride in 190 ml of toluene was added dropwise over 1 hour. This was warmed to room temperature, was stirred for further 1 hour and was washed with water, followed by removal of the solvent under reduced pressure. The residue was mixed with methanol and was further mixed with water with stirring under ice-cooling, to yield crystals of the target compound. The crystals were collected by filtration through a Nutsche funnel, were rinsed with a mixture of distilled water and methanol and were dried, to yield 38.1 g (87 mmol) of tri-tert-butyl ester of 1,3,5-adamantanetricarboxylic acid in a yield of 90%.

[NMR Spectral Data] $^1$H-NMR (CDCl$_3$) δ (ppm): 1.43 (s, 27H), 1.85 (m, 6H), 2.03 (m, 6H), 2.31 (m, 1H) $^{13}$C-NMR (CDCl$_3$) δ (ppm): 27.90, 28.02, 37.11, 39.16, 41.32, 79.73, 176.44

EXAMPLE 4

Preparation of tris(methoxyethyl)ester of 1,3,5-adamantanetricarboxylic acid

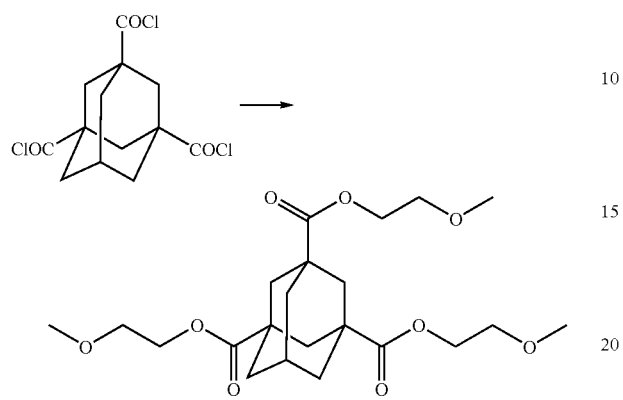

In a 500-ml flask equipped with a stirrer, a thermometer and a dropping funnel were placed 36.9 g (485 mmol) of 2-methoxyethanol, 38.4 g (485 mmol) of pyridine and 140 ml of toluene. To the stirred mixture under ice-cooling in a nitrogen atmosphere, 31.4 g (97 mmol) of 1,3,5-adamantanetricarbonyl trichloride in 190 ml of toluene was added dropwise over 1 hour. This was warmed to room temperature, was stirred for further 1 hour and was washed with water, 1 N aqueous hydrochloric acid, and 10% aqueous sodium carbonate solution, and the solvent was removed under reduced pressure, to yield 38.5 g (87 mmol) of tris(methoxyethyl)ester of 1,3,5-adamantanetricarboxylic acid in a yield of 90%.

[NMR Spectral Data] $^1$H-NMR (CDCl$_3$) δ (ppm): 1.86 (m, 6H), 2.05 (m, 6H), 2.30 (m, 1H), 3.38 (s, 9H), 3.59 (m, 6H), 4.23 (m, 6H) $^{13}$C-NMR (CDCl$_3$) δ (ppm): 27.84, 36.97, 38.93, 41.33, 58.97, 63.64, 70.39, 175.90

EXAMPLE 5

Preparation of 1,3,5-tris(1-pyrrolidinylcarbonyl)adamantane

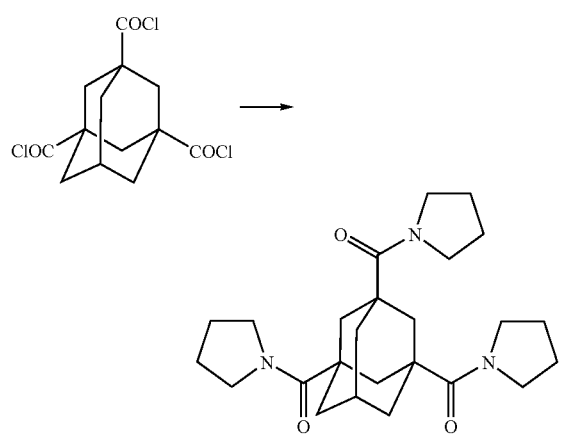

In a 500-ml flask equipped with a stirrer, a thermometer and a dropping funnel were placed 34.5 g (485 mmol) of pyrrolidine, 38.4 g (485 mmol) of pyridine and 140 ml of methylene chloride. To the stirred mixture under ice-cooling in a nitrogen atmosphere, 31.4 g (97 mmol) of 1,3,5-adamantanetricarbonyl trichloride in 190 ml of toluene was added dropwise over 1 hour. This was warmed to room temperature, was stirred for further 1 hour and was washed with water, 1 N aqueous hydrochloric acid, and 10% aqueous sodium carbonate solution, and the solvent was removed under reduced pressure, to yield 37.2 g (87 mmol) of 1,3,5-tris(1-pyrrolidinylcarbonyl)adamantane in a yield of 90%.

Infrared absorption spectral data (cm$^{-1}$): 2900, 1620, 1450, 1370, 1160, 1050 MS: 428 (M+H)

EXAMPLE 6

Preparation of 1,3,5-adamantanetricarboxylic acid N,N-diethylamide[1,3,5-tris(N,N-diethylcarbamoyl) adamantane]

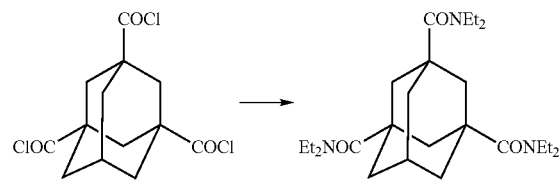

In a 500-ml flask equipped with a stirrer, a thermometer and a dropping funnel were placed 35.5 g (485 mmol) of diethylamine, 38.4 g (485 mmol) of pyridine and 140 ml of methylene chloride. To the stirred mixture under ice-cooling in a nitrogen atmosphere, 31.4 g (97 mmol) of 1,3,5-adamantanetricarboxylic trichloride in 190 ml of toluene was added dropwise over 1 hour. This was warmed to room temperature, was stirred for further 1 hour and was washed with water, 1 N aqueous hydrochloric acid, and 10% aqueous sodium carbonate solution, and the solvent was removed under reduced pressure, to yield 35.8 g (82 mmol) of 1,3,5-adamantanetricarboxylic acid N,N-diethylamide in a yield of 85%.

Infrared absorption spectral data (cm$^{-1}$): 2900, 1620, 1450, 1370, 1160, 1050 MS: 434 (M+H)

EXAMPLE 7

In 100 g of mesitylene were dissolved 2.48 g (8 mmol) of trimethyl ester of 1,3,5-adamantanetricarboxylic acid prepared in Example 1 and 6.42 g (12 mmol) of 3,3'-diaminobenzidinetetracyclohexanoimine [N,N',N'',N'''-tetracyclohexylidene-3,4,3',4'-biphenyltetramine] prepared in Preparation Example 1 at room temperature in a nitrogen atmosphere, to yield a coating liquid having a monomer concentration of 8.2% by weight. After filtrating through a filter with a pore size of 0.1 μm, the coating liquid was applied to an 8-inch silicon wafer by spin coating. This was heated at 300° C. in a nitrogen atmosphere for 30 minutes and was then heated at 400° C. for further 30 minutes, to form a film. The infrared absorption spectrum of the resulting polymer film was determined. The result is shown in FIG. 1, verifying that the target crosslinked polybenzazole film was formed. The film had a thickness of 300 nm.

Infrared absorption spectral data (cm$^{-1}$):
805 (m), 1280 (m), 1403 (m), 1450 (s), 1522 (w), 1625 (w), 2857 (s), 2928 (s), 3419 (w)

COMPARATIVE EXAMPLE 1

A coating liquid was prepared by the procedure of Example 7, except using equal amounts of 1,3,5-adamantanetricarboxylic acid and 3,3'-diaminobenzidine instead of trimethyl ester of 1,3,5-adamantanetricarboxylic acid and N,N',N'',N'''-tetracyclohexylidene-3,4,3',4'-biphenyltetramine, respectively. However, the components were not sufficiently dissolved in the solvent (mesitylene). Accordingly, another coating liquid having a monomer concentration of 1.2% by weight was prepared by the procedure of Example 7, except using 0.54 g (2 mmol) of 1,3,5-adamantanetricarboxylic acid and 0.64 g (3 mmol) of 3,3'-diaminobenzidine. A polymer film was formed by the procedure of Example 7, except using the above-prepared coating liquid. The infrared absorption spectrum of the resulting polymer film was determined, verifying that the target crosslinked polybenzazole film was formed. The film had a thickness of less than 20 nm.

COMPARATIVE EXAMPLE 2

In a flask equipped with a stirrer and a condenser were placed 5.37 g (20 mmol) of 1,3,5-adamantanetricarboxylic acid, 6.43 g (30 mmol) of 3,3'-diaminobenzidine and 100 g of a polyphosphoric acid, followed by heating and stirring at 200° C. in a nitrogen atmosphere for 12 hours. After cooling, the reaction mixture was mixed with water, the precipitated solid was collected by filtration and was washed with aqueous sodium hydrogen carbonate solution, water, and methanol, to yield a polybenzimidazole as a solid. An attempt was made to dissolve the solid polybenzimidazole in a solvent, N-methylpyrrolidone (NMP), but was failed. Thus, a thin film could not be formed by spin coating, and a target thin film was not prepared.

While the present invention has been described with reference to what are presently considered to be the preferred embodiments, it is to be understood that the invention is not limited to the disclosed embodiments. On the contrary, the invention is intended to cover various modifications and equivalent arrangements included within the spirit and scope of the appended claim. The scope of the following claim is to be accorded the broadest interpretation so as to encompass all such modifications and equivalent structures and functions.

What is claimed is:

1. An adamantanetricarboxylic acid derivative represented by following Formula (1):

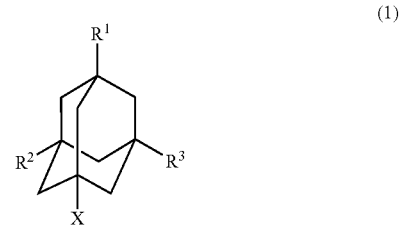

wherein X is a hydrogen atom or a hydrocarbon group; and $R^1$, $R^2$ and $R^3$ may be the same as or different from one another and are each a carboxyl group which may be protected by a protecting group, or a carbonyl halide group, wherein at least one of $R^1$, $R^2$ and $R^3$ is a carbonyl halide group or a carboxyl group which is protected by a protecting group selected from the group consisting of alkoxy groups, cycloalkyloxy groups, tetrahydrofuranyloxy groups, tetrahydropyranyloxy groups, aryloxy groups, aralkyloxy groups, trialkylsilyloxy groups, amino groups which may have one or more substituents, cyclic amino groups, hydrazino groups which may have one or more substituents, and acyloxy groups.

* * * * *